(12) United States Patent
Escano

(10) Patent No.: US 6,423,052 B1
(45) Date of Patent: Jul. 23, 2002

(54) TORQUE ABSORBING CATHETER

(75) Inventor: Arnold Escano, Santa Clara, CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 125 days.

(21) Appl. No.: 09/641,735

(22) Filed: Aug. 18, 2000

(51) Int. Cl.$^7$ ............................................. A61M 25/10
(52) U.S. Cl. ..................................... 604/523; 604/96.01
(58) Field of Search ........................... 604/96.01, 508, 604/509, 510, 270, 523, 528

(56) References Cited

U.S. PATENT DOCUMENTS

| | | | |
|---|---|---|---|
| 3,780,740 A | * 12/1973 | Rhea ........................... 604/270 |
| 4,790,831 A |   12/1988 | Skribiski |
| 4,857,046 A | *  8/1989 | Stevens et al. ................ 604/22 |
| 4,991,602 A |    2/1991 | Amplatz et al. |
| 5,037,391 A |    8/1991 | Hammerslag et al. |
| 5,322,064 A |    6/1994 | Lundquist |
| 5,429,597 A | *  7/1995 | DeMello et al. ....... 604/103.09 |
| 5,693,015 A |   12/1997 | Walker et al. |
| 5,695,111 A | * 12/1997 | Nanis et al. ................. 228/206 |
| 5,807,236 A | *  9/1998 | Bacich et al. ................ 600/104 |
| 5,836,925 A | * 11/1998 | Soltesz ........................ 604/264 |
| 5,902,254 A |    5/1999 | Magram |
| 5,908,405 A |    6/1999 | Imran et al. |
| 5,916,227 A | *  6/1999 | Keith et al. .................... 604/22 |
| 5,938,670 A | *  8/1999 | Keith et al. .................. 606/159 |
| 5,951,494 A |    9/1999 | Wang et al. |
| 5,957,672 A | *  9/1999 | Aber ........................ 384/907.1 |
| 6,051,014 A | *  4/2000 | Jang ......................... 604/96.01 |
| 6,142,987 A | * 11/2000 | Tsugita ........................ 604/500 |

* cited by examiner

Primary Examiner—William E. Tapolcai
(74) Attorney, Agent, or Firm—Blakely, Sokoloff, Taylor & Zafman LLP

(57) ABSTRACT

A torque absorbing catheter having one or more torque absorbing bearings disposed at the distal end thereof. The bearings are larger than the outer diameter of any flexible region of the catheter sought to be protected from torque as the catheter is inserted through a tortuous body lumen. As the catheter is inserted through a body lumen, the bearings are rotable therein and the catheter shaft is simultaneously rotable within a bearing lumen of the bearings. This prevents transfer of torque from bearing to shaft and catheter. The invention is particularly adept at preventing torque from deforming the shape and character of a particularly flexible catheter region such as a balloon.

24 Claims, 2 Drawing Sheets

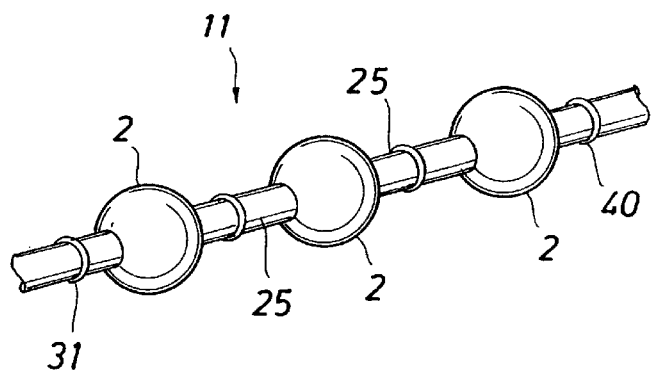
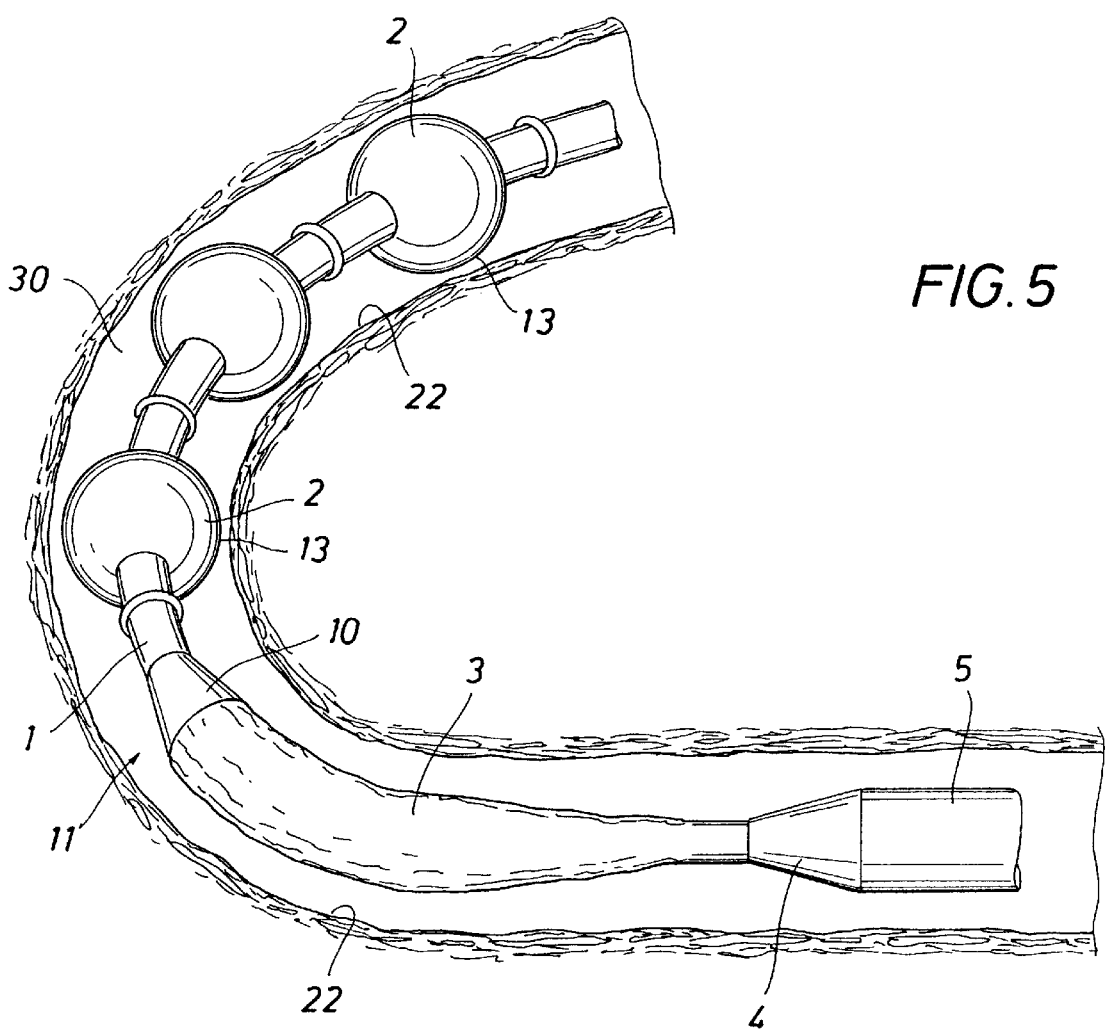

TORQUE ABSORBING CATHETER

BACKGROUND OF THE INVENTION

The present invention relates to catheters of any type meant for insertion through a body lumen such as vasculature. In particular, the present invention can effectively transmit torque in a desired manner along a catheter or other device for a body lumen having high profile.

BACKGROUND OF THE RELATED ART

In the last several years the field of minimally invasive surgery has grown exponentially. In particular, catheterization procedures such as angioplasty (including Percutaneous Transluminal Coronary Angioplasty) have become widely accepted norms. Even more complex procedures such as the placement of aneurysm grafts are accomplished by way of catheterization.

Due to the increased popularity of minimally invasive catheterization procedures, catheters have become more complex in order to accommodate additional catheter features needed for more complex procedures. Additional catheter features often result in catheters which are relatively large in diameter (i.e. high profile) and thus more susceptible to torque from a body lumen, such as vasculature, as the catheter is inserted through the body lumen.

One example of a complex catheter is the angioplasty catheter. Angioplasty is performed with an angioplasty catheter having an inflatable balloon at its distal end. The angioplasty catheter may be equipped with multiple lumen for inflation, deflation, guidewire access, visualization dye access, and for other purposes. The lumen will generally be located through a catheter shaft. The shaft will be of a sufficient profile to accommodate the various lumen. Such multi-lumen catheters are relatively large and stiff and therefore subject the associated flexible inflatable balloon to a considerable amount of torque upon insertion through a body lumen, in this case vasculature.

In order to insert a catheter such as the angioplasty catheter to a desired vessel location, the guidewire will first be inserted and steered to the site of a stenosis. Subsequently, the angioplasty catheter is inserted over the guidewire. The angioplasty catheter is steered through vasculature to the site of the stenosis with the object of placing the deflated balloon across the stenosis so that it may then be inflated to compress the stenosis against vessel walls.

Unfortunately, vasculature is often quite tortuous and of limited diameter. As the angioplasty catheter tightly forces its way through the vasculature, it is Subjected to vessel walls which act to wind and distort the angioplasty catheter as it makes various turns there through. The inflatable balloon, having more flexible walls than other portions of the angioplasty catheter, will distort and absorb the torque imposed by the tortuous vasculature. By the time the inflatable balloon reaches its destination it may be twisted and creased. This distortion will hamper the effectiveness of the angioplasty compression when the inflatable balloon is later inflated.

A similarly complex catheter procedure involves the placement of an aneurysm graft within an abdominal aneurysm. Placement of an aneurysm graft will involve an intricate delivery system, referred to here as an aneurysm graft catheter. The aneurysm graft catheter is constructed similarly to the angioplasty catheter with a balloon near its distal end. However, the aneurysm graft catheter is even larger and more complex. Proximal of the balloon, the catheter is equipped with additional obtrusive features such as a jacket guard. The jacket guard is proximal to the superior end of a capsule which houses an aneurysm graft. The balloon must be of sufficient size to aid in the deployment of the aneurysm graft from the capsule within a bifurcated aneurysm. The size of the balloon and the presence of a large diameter capsule housing an aneurysm graft increases the amount of torque which is endured by the catheter as it is forced through a tortuous vessel to the site of an aneurysm. As a result, the balloon of the aneurysm graft catheter is subjected to a significant amount of torque and again susceptible to distortion and creasing in reaching its destination.

As indicated in both of the above catheter procedure examples, torque control is vital to effective catheter placement and use. This is especially true where balloon or other flexible catheter features are present which are subject to torque effects. However, in addition to torque control, the catheter may display a degree of flexibility and be limited in size and stiffness in order to prevent damage to vasculature as the catheter is inserted there through. Unfortunately, more flexibility exhibited by the catheter generally equates to less torque control. Therefore what is needed is a catheter having able to overcome such torque problems and having advantages over prior art catheters.

SUMMARY OF THE INVENTION

The present invention provides a catheter. The catheter is equipped with a torque absorbing bearing disposed about a shaft of the catheter near a distal portion of a flexible region of the catheter. The catheter may be equipped with a plurality of torque absorbing bearings. The plurality includes a proximal torque absorbing bearing immediately distal of the flexible region.

A method of catheterization is also provided. A catheter having a torque absorbing bearing may be inserted through a tortuous body lumen.

A method of manufacturing a torque absorbing catheter is also provided. An embodiment is described in which a catheter shaft is molded and a torque absorbing bearing placed about the shaft. A bearing ring stop is placed adjacent the torque absorbing bearing.

BRIEF DESCRIPTION OF THE DRAWINGS

FIG. 4 is a view of an embodiment of the present invention in which a plurality of torque absorbing bearings are located at the distal end of a catheter.

FIG. 5 shows a torque absorbing catheter within tortuous vasculature and having a plurality of torque absorbing bearings.

DETAILED DESCRIPTION OF THE INVENTION

While the background of the present invention is described with reference to certain balloon catheters (i.e. angioplasty and aneurysm placement catheters), the invention is applicable to any catheter meant for insertion through a tortuous lumen. This would include angiography, radiation, stent placement catheters, etc. The invention is particularly useful when the catheter involved has obtrusive catheter features having outer walls of increased flexibility, such as a balloon catheter.

The following description makes reference to numerous specific details in order to provide a thorough understanding of the present invention. However, each specific detail need not be employed to practice the present invention. Additionally, well-known details, such as particular materials or methods, have not been described in order to avoid obscuring the present invention.

Figure 1:
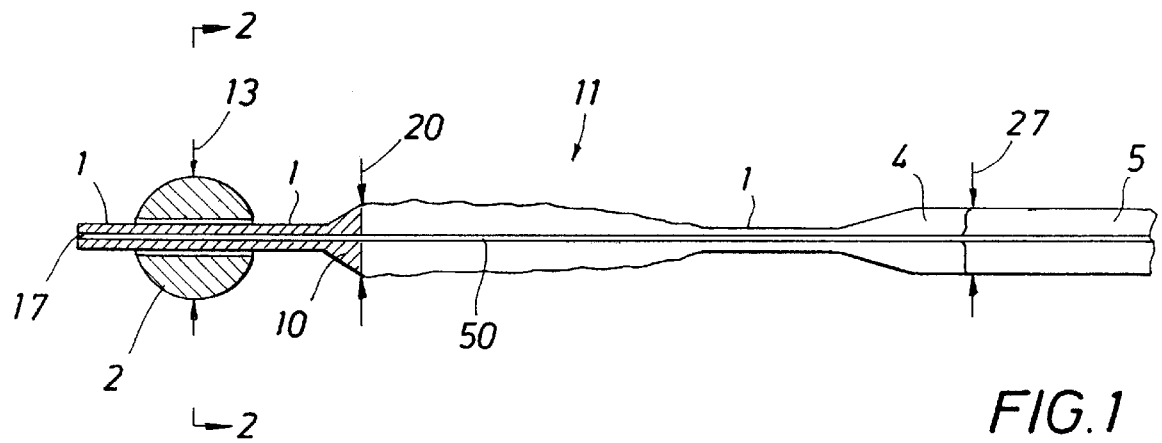
FIG. 1 is a perspective view of an overall torque absorbing catheter system of an embodiment of the present invention.

With reference to FIG. 1, a torque absorbing catheter system is shown. The catheter 11 is comprised of an elongated shaft 1 having a central lumen 50 there through. Part of the central lumen may consist of a guidewire lumen 17 terminating at the distal end of the catheter 11 (i.e. an "over the wire" catheter configuration). The particular catheter 11 shown allows placement of an aneurysm graft (not shown). However, this particular type of catheter 11 is not essential. Several obtuse features are found disposed on the catheter 11 giving the catheter 11 a relatively high profile. These features include a capsule 5 meant for housing an aneurysm graft. Distal of the capsule 5 is a jacket 4 which aids in advancement of the capsule 5 through vasculature and guards the capsule 5 to help avoid unintended graft deployment. A balloon 3 is disposed distal of the jacket 4.

The balloon 3 allows deployment of the aneurysm graft once the catheter 11 is advanced to the aneurysm site. That is, the balloon 3 may be inflated to secure a distal portion of the catheter 11 within vasculature. Subsequently, the jacket 4 and capsule 5 may be disengaged to allow deployment of the graft from within the capsule 5. The balloon 3 is more flexible than the catheter shaft 1, the jacket 4, and the capsule 5. Thus, the catheter 11 is not only relatively high in profile, but it also has a portion high in flexibility. This flexibility allows the balloon 3 to be inflated to the desired level but also leaves the catheter 11 potentially susceptible to torque at the location of the balloon 3. The potential susceptibility to torque at this location is increased due to the generally high profile of the catheter 11. However, the present invention allows such a catheter 11 to avoid the effects of torque in spite of the high profile and increased flexibility.

The balloon 3 terminates at a distal portion as a stem 10. The stem 10, is not necessarily as flexible as the remainder of the balloon 3 as its shape tapers into the shaft 1 and it need not inflate in the manner of the balloon 3.

Distal of the balloon 3 is a torque absorbing bearing 2. The bearing 2 preferably has an outer diameter 13 larger than the more flexible portions of the catheter 11. As mentioned above, the balloon 3 is a more flexible portion of the catheter 11 of the embodiment shown. Therefore, the bearing 2 has an outer diameter 13 preferably somewhat larger than the stem 10 outer diameter 20. This helps promote contact between vessel walls and the bearing 2 in lieu of contact between vessel walls and the balloon 3 as the catheter 11 is advanced through a tortuous vessel (not shown) with an un-inflated balloon 3. The bearing 2 may be sized to have an outer diameter 13 larger than any feature to be shielded from vessel contact. In fact, if no significantly profiled catheter 11 body features are present other than the shaft 1 and the bearing 2, the bearing 2 will have the effect of simply reducing torque effects upon the catheter 11 at the distal portion of the shaft 1. However, the more proximal the feature or shaft 1, the less shielding is available from the outer diameter 13. Therefore, if other portions of the catheter are of concern such as additional obtuse features which have a high degree of flexibility, another bearing may be placed immediately adjacent such features as well (not shown). However, the capsule 5 and jacket 4 of the embodiment shown are not of such concern.

The bearing 2 shown may have an outer diameter 13 larger than features at a more proximal portion of the catheter 11 in order to aid in catheter 11 insertion. For example, the bearing 2 shown may have an outer diameter 13 larger than the capsule jacket diameter 27 so that the stress of contact between vessel walls and the jacket 4 and capsule 5 is lessened allowing easier insertion of the catheter 11. However, if any of the obtuse features have a sufficiently high profile, the bearing 2 should not have an outer diameter 13 larger than such profile if this would subject vasculature to potential damage upon catheter 11 insertion and advancement. In such cases, sufficiently large profile features should also be relatively short in length and less flexible, thus capable of withstanding torque from vasculature without significantly distorting. This may be the case with the jacket 4 and capsule 5 of the catheter 11 shown.

Figure 2:
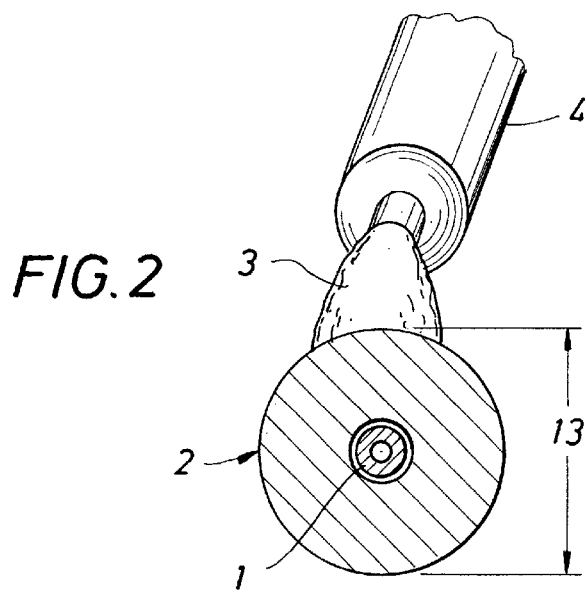
FIG. 2 is a front sectional view the torque absorbing bearing shown in FIG. 1.
Figure 3:
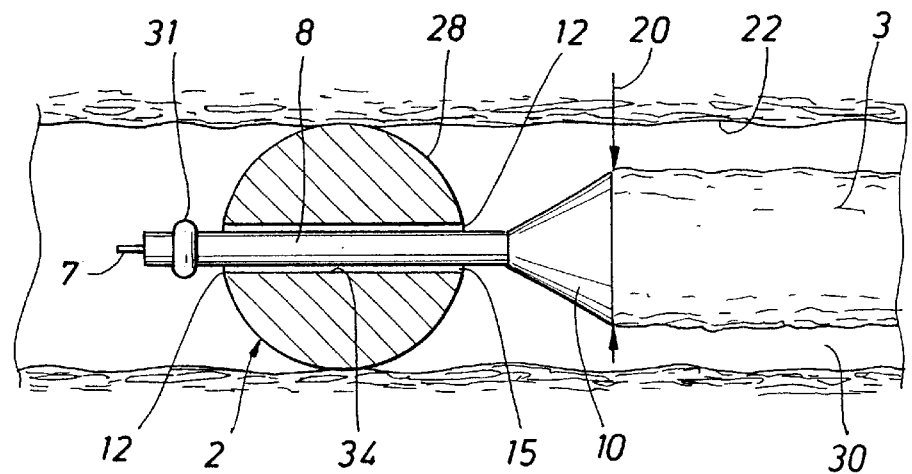
FIG. 3 is a side sectional view of the torque absorbing bearing of FIG. 2 within vasculature.

With reference to FIGS. 2 and 3, cross sections of the bearing 2 are shown. The bearing 2 is rotable both about the shaft 1 and within the vessel lumen 30 once placed therein. The bearing 2 is comprised of stainless steel, polyethylene, or any sufficiently solid material being biocompatible, stress and moisture resistant, and having a relatively minimal coefficient of friction. In order to enhance rotability, the bearing 2 may have hydrophilic coatings in the form of an outer layer 28 and upon an inner lumen wall 34.

The bearing 2 is large enough to obstruct the view of the stem 10 when viewed from the front. When placed within a vessel lumen 30, the bearing 2 contacts the vessel wall 22 in a manner that discourages contact between the vessel wall 22 and the balloon 3. Contact is also discouraged between the vessel wall 22 and the shaft 1 distal of the balloon 3. The bearing 2 is shown having an outer diameter 13 larger than the stem outer diameter 20. An orifice 12 runs through the bearing 2 forming a beating lumen 15 with inner lumen wall 34. The shaft 1 extends through the bearing lumen 15 and provides a distal bearing ring stop 31 adjacent the bearing 2 at a more distal portion of the catheter 11. A bearing ring stop may also be provided adjacent the bearing 2 at a more proximal portion of the catheter 11 (not shown).

Distal bearing ring stop 31 may be formed simultaneously with the shaft 1. This prevents deformation of the guidewire 7 or other lumen which may occur if the distal bearing ring stop 31 is a separate structure merely molded to the shaft 1 after both have been formed. Alternatively, the stop 31 may be manufactured following molding of the shaft 1. However, in this case, the stop 31 should be formed directly from the shaft 1 itself. This could be accomplished by heating the shaft 1 at a particular location and compressing it from a distal and a proximal end toward the heated location until the stop 31 is formed. In such a situation, the central, guidewire 7, or any other present lumen, should be temporarily supported by a wire filler to prevent lumen deformation at the site of the heated location.

The distal bearing ring stop 31 is larger than the orifice 12 thereby preventing the bearing 2 from disengaging the shaft 1 by moving toward a more distal portion of the shaft 1. The stem 10 prevents the bearing from moving toward and over the balloon 3. The bearing 2 is free to travel along the shaft 1 between the distal bearing ring stop 31 and the stem 10. If desirable this distance may be shortened or lengthened by altering the positioning of the distal bearing ring stop 31.

Alternatively, a proximal bearing ring stop (not shown) may be placed adjacent the bearing 2 at a more distal portion of the catheter 11 in order to define the range of bearing 2 movement over the shaft 1.

As mentioned, the outer layer 28 is a hydrophilic coating. This promotes rotation of the bearing 2 within the vessel lumen 30 in spite of making forceful contact with the vessel wall 22. Likewise, the inner lumen wall 34 of the bearing 2 has a hydrophilic coating which further enhances freedom of movement between the shaft 1 and the inner lumen wall 34. That is, once advancement through the vessel lumen 30 proceeds the bearing 2 allows the shaft 1 to circumferentially rotate within the bearing lumen 15 and avoid the torque effects of a tortuous vessel. The bearing 2 itself avoids torque to a certain degree due to its outer layer 28 having a hydrophilic coating. The torque avoided here is torque which will not be undesirably transferred to the shaft 1 or other portions of the catheter. To the extent that torque is not avoided by rotation of the bearing 2 due to its outer layer 28 composition, it may be avoided by the ability of the shaft 1 to rotate within the bearing lumen 15 without itself twisting or causing other catheter features such as the balloon 3 to twist. The ability of the shaft 1 to rotate within the bearing lumen 15 is further enhanced by the amount of distance between the shaft 1 and the inner lumen wall 34. The distance is large enough to prevent tight contact between the shaft 1 and the inner lumen wall 34. The ability of the shaft 1 to rotate within the bearing lumen 15 without twisting the balloon 3 is dependent upon there being sufficient distance between the balloon 3 and vessel wall 22 as provided by the bearing 2 and its outer diameter 13 (see FIG. 1).

Referring to FIGS. 4 and 5, the distal end of the catheter 11 is shown with a plurality of bearings 2 disposed thereat. A plurality of bearings 2 may provide more stabilized vascular expansion as the catheter 11 advances through the vasculature. The bearings 2 are separated by shaft bearing gaps 25 which are of a distance adequate to allow sufficient flexure of the shaft 1 as it is advanced through tortuous vasculature. The bearings 2 must be spaced apart to avoid contact with one another. Otherwise, bending of the shaft 1 at the site of the bearings 2 will be compromised by the bearings 2 as they contact one another. In order to maintain proper bearing spacing, both a distal 31 and a proximal 40 bearing ring stop are desirable.

I claim is:

1. A catheter comprising:
   an elongated shaft having a first flexible region with a first outer diameter; and
   a torque absorbing bearing disposed about a distal portion of said shaft adjacent said first flexible region, said torque absorbing bearing having a second outer diameter larger than said first outer diameter.

2. The catheter of claim 1 wherein said torque absorbing bearing is comprised of a material selected from the group consisting of stainless steel and polyethylene.

3. The catheter of claim 1 wherein said torque absorbing bearing further comprises an outer layer of hydrophilic coating to promote rotability of said torque absorbing bearing within vasculature when inserted there through.

4. The catheter of claim 1 further comprising:
   a second flexible region of said shaft at a more proximal portion of said catheter than said first flexible region; and
   a second torque absorbing bearing disposed on said shaft between said first and said second flexible regions.

5. The catheter of claim 1 wherein said torque absorbing bearing further comprises:
   a bearing lumen there through; and
   an inner lumen wall of said bearing lumen, said inner lumen wall circumferentially surrounding said shaft, said shaft rotable within said bearing.

6. The catheter of claim 5 wherein said torque absorbing bearing further comprises a hydrophilic coating upon said inner lumen wall to provide rotability of said shaft within said torque absorbing bearing.

7. The catheter of claim 5 wherein said inner lumen wall and said shaft are distanced to provide rotability of said shaft within said torque absorbing bearing.

8. The catheter of claim 5 further comprising:
   a distal orifice of said bearing lumen; and
   a distal bearing ring stop circumferentially about a distal portion of said shaft adjacent said torque absorbing bearing, said distal bearing ring stop being larger than said distal orifice.

9. The catheter of claim 5 further comprising:
   a proximal orifice of said bearing lumen; and
   a proximal bearing ring stop circumferentially about a proximal portion of said shaft adjacent said torque absorbing bearing, said proximal bearing ring stop being larger than said proximal orifice.

10. The catheter of claim 5 wherein said first flexible region further comprises a balloon terminating distally in a stem which tapers distally into said shaft.

11. The catheter of claim 10 further comprising:
    a proximal orifice of said bearing lumen;
    a distal orifice of said bearing lumen; and
    a distal bearing ring stop about said shaft distal of said torque absorbing bearing, said distal bearing ring stop being larger than said distal orifice, said stem being larger than said proximal orifice.

12. The catheter of claim 1 further comprising a high profile region being rigid to avoid torque of vasculature as said torque absorbing catheter is inserted there through.

13. The catheter of claim 12 wherein said high profile region has no torque absorbing bearing immediately adjacent thereto.

14. A catheter comprising:
    an elongated shaft having a flexible region with a first outer diameter;
    a plurality of torque absorbing bearings disposed at a distal portion of said shaft adjacent said flexible region; and
    a proximal torque absorbing bearing of said plurality of torque absorbing bearings, said proximal torque absorbing bearing immediately adjacent said flexible region and having a second outer diameter larger than said first outer diameter.

15. The catheter of claim 14 further comprising shaft bearing gaps between each adjacent torque absorbing bearing of said plurality of torque absorbing bearings, said shaft bearing gaps to permit adequate flexure of said shaft when said torque absorbing catheter is advanced through a tortuous vessel.

16. The catheter of claim 14 wherein each said torque absorbing bearing includes a distal orifice, said catheter further comprising a plurality of distal bearing ring stops circumferentially about said shaft, each said distal bearing ring stop being adjacent a torque absorbing bearing of said plurality of torque absorbing bearings, each distal bearing ring stop being larger than each said distal orifice adjacent thereto.

17. The catheter of claim 14 wherein each said torque absorbing includes a proximal orifice, said catheter further comprising a plurality of proximal bearing ring stops circumferentially about said shaft, each said proximal bearing ring stop being adjacent a torque absorbing bearing of said plurality of torque absorbing bearings, each proximal bearing ring stop being larger than each said proximal orifice adjacent thereto.

18. The catheter of claim 14 further comprising:
   a proximal-most bearing of said plurality of torque absorbing bearings; and
   a distal-most bearing of said plurality of torque absorbing bearings, said proximal-most bearing being larger than said distal-most bearing.

19. A method of catheterization comprising:
   providing a catheter with a flexible region and a torque absorbing bearing at a distal portion of said catheter; and
   advancing said catheter through a tortuous body lumen to treat a patient, said torque absorbing bearing to help avoid torque effects upon said flexible region as said catheter advances through said tortuous body lumen.

20. The method of claim 19 wherein said flexible region comprises a balloon.

21. A method of manufacturing a torque absorbing catheter comprising:
   molding a catheter shaft; and
   providing a torque absorbing bearing circumferentially about said catheter shaft.

22. The method of claim 21 further comprising disposing a bearing ring stop circumferentially about said catheter shaft adjacent said torque absorbing bearing.

23. The method of claim 22 wherein said disposing occurs simultaneous with said molding.

24. The method of claim 22 wherein said disposing further comprises:
   placing a wire filler within a lumen of said catheter shaft;
   heating a section of said catheter shaft; and
   forcing a distal end and a proximal end of said catheter shaft toward said section in order to form said bearing ring stop at said section.

\* \* \* \* \*